United States Patent
Han et al.

(10) Patent No.: US 8,388,127 B2
(45) Date of Patent: Mar. 5, 2013

(54) VISION ASSISTANCE DEVICE HAVING CONDUCTIVE TRANSPARENT THIN FILM

(75) Inventors: Chang-Soo Han, Daejeon (KR);
Jin-Won Song, Daejeon (KR);
Joon-Dong Kim, Daejeon (KR)

(73) Assignee: Korea Institute of Machinery & Materials, Daejeon (KR)

( * ) Notice: Subject to any disclaimer, the term of this patent is extended or adjusted under 35 U.S.C. 154(b) by 239 days.

(21) Appl. No.: 12/993,866

(22) PCT Filed: May 21, 2009

(86) PCT No.: PCT/KR2009/002682
§ 371 (c)(1),
(2), (4) Date: Nov. 22, 2010

(87) PCT Pub. No.: WO2009/142447
PCT Pub. Date: Nov. 26, 2009

(65) Prior Publication Data
US 2011/0069274 A1    Mar. 24, 2011

(30) Foreign Application Priority Data
May 22, 2008    (KR) .................... 10-2008-0047698

(51) Int. Cl.
*G02C 11/08*    (2006.01)

(52) U.S. Cl. ............. 351/62; 977/748; 977/833
(58) Field of Classification Search ........... 351/41, 351/62, 158; 2/435; 359/512; 977/742, 977/748, 832–834, 950
See application file for complete search history.

(56) References Cited

U.S. PATENT DOCUMENTS

| 4,209,234 A | 6/1980 | McCooeye |
| 5,471,036 A * | 11/1995 | Sperbeck ............... 219/522 |
| 2006/0188721 A1 * | 8/2006 | Irvin et al. ............. 428/402 |

FOREIGN PATENT DOCUMENTS

| DE | 27 18 679 | 11/1978 |
| DE | 20 2005 013 822 | 9/2006 |
| DE | 10 2007 004 953 | 7/2008 |

* cited by examiner

*Primary Examiner* — Huy K Mai
(74) *Attorney, Agent, or Firm* — Lexyoume IP Meister, PLLC.

(57) ABSTRACT

A vision assistance device includes a lens based on a transparent material, a conductive transparent thin film contacting the lens and containing carbon nanotubes, electrodes electrically connected to the conductive transparent thin film, and a portable power supply electrically connected to the electrodes. The vision assistance device prevents fogging and retains heat.

16 Claims, 4 Drawing Sheets

VISION ASSISTANCE DEVICE HAVING CONDUCTIVE TRANSPARENT THIN FILM

TECHNICAL FIELD

The present invention relates to a vision assistance device having a conductive transparent thin film, and more particularly, to a vision assistance device coated with a conductive transparent thin film containing carbon nanotubes.

BACKGROUND ART

A conductive transparent thin film may be formed with various materials, such as indium tin oxide (ITO) which has been traditionally used most extensively, and a carbon-based material like a conductive polymer and carbon nanotubes which are increasingly being used.

An oxide-based material such as ZnO, $SnO_2$, $In_2O_3$, and $CdSnO_4$ may also be used for that purpose. Furthermore, a metallic material such as Au, Al, and Ag, or fluorine, may be partially added to the thin film formation material so as to enhance the conductivity thereof.

For example, fluorine-doped tin oxide (FTO), aluminum-doped zinc oxide (AZO), etc., are currently being used for that purpose. The thin film refers to a conductive film with a thickness of 10 μm or less.

A conductive organic polymer may be taken as another transparent conductive material. The conductive polymer and conductive plastic have been developed since 1970. A polymer-based conductive material such as polyaniline, polythiophene, polypyrrole, and polyacetylene may be used.

Studies on the formation of a conductive film where a carbon-based material such as carbon nanotubes and carbon black are deposited into or on the surface of a transparent substrate have recently been actively pursued.

Such a conductive transparent thin film may be utilized in a field emission display, an electrostatic shield, a touch screen, an LCD electrode, a heater, a functional optical film, a composite material, chemical and bio sensors, a solar cell, an energy storage material, an electronic device, etc.

Particularly, carbon nanotubes may be effectively used as an electrode material for a flexible display or a flexible solar cell.

With the ITO which has been conventionally used as a transparent heater, it is common to deposit it on the surface of a substrate under a vacuum atmosphere, and this results in a high processing cost and complicated processing steps. Furthermore, with the ITO, the target materials to be deposited therewith are limited in selection, and it is difficult to arbitrarily select the proper optical material.

When wearing goggles or glasses when participating in sports such as skiing, fogging frequently occurs in winter due to a temperature difference. In order to prevent such fogging, it is well known to coat an anti-fog film on the lens, but the fogging cannot be completely prevented even with the usage of such a film. And as time passes by, the anti-fog film is liable to be deteriorated in function.

In particular, when wearing goggles when participating in sports such as skiing, the fogging frequently occurs due to the difference between the inner temperature of the goggles and the goggle lens. When such fogging occurs when moving at a high speed, visibility problems occur such that safety may be deteriorated.

The above information disclosed in this Background section is only for enhancement of understanding of the background of the invention and therefore it may contain information that does not form the prior art that is already known in this country to a person of ordinary skill in the art.

DISCLOSURE OF INVENTION

Technical Problem

The present invention has been made in an effort to provide a vision assistance device with a conductive transparent thin film having advantages of preventing fogging while exhibiting high transparency and thermal efficiency.

Technical Solution

An exemplary embodiment of the present invention provides a vision assistance device with a transparent heater. The vision assistance device includes a lens based on a transparent material, a conductive transparent thin film surface-contacting the lens and containing carbon nanotubes, electrodes electrically connected to the conductive transparent thin film, and a portable power supply electrically connected to the electrodes.

The conductive transparent thin film may have transparency of 10% or more, and electrical resistance of $1\Omega$ to $10^5\Omega$.

The carbon nanotubes may be adsorbed with any one material selected from the group consisting of a metal oxide, a semiconductor, a metal, a polymer, and a semiconductor oxide, or a combination thereof. The lens may be formed with glass or a polymer.

The electrode may be installed at a location where the angle of a line proceeding from the eye center of the lens wearer to the vertical center of the lens to the line proceeding from the eye center of the lens wearer to the electrode reaches 10° or more.

The portable power supply may be electrically connected to the electrode via an electric wire. The portable power supply may be fitted to a case and electrically connected to the electric wire via the case. The electric wire may be connected to the electrode via a conductive adhesive. The portable power supply may be formed as a portable solar battery.

The electrodes may be spaced apart from each other by a distance in the vertical direction of the lens. The electrodes may be horizontally symmetrical to each other with respect to a vertical center line of the lens. The electrode may have electrode protrusions protruded to the inner side of the lens.

The conductive transparent thin film may be attached to the lens via a transparent adhesive layer, and a switch may be installed between the electrode and the portable power supply.

An insulating transparent coating film may be formed on the conductive transparent thin film, and a conductive adhesive layer may be formed between the conductive transparent thin film and the electrode.

Advantageous Effects

With the conductive transparent thin film containing carbon nanotubes according to the exemplary embodiment of the present invention, the temperature is increased at a very high speed and maintained to be constant compared with an Ag-based thermal wire or a thick-filmed heater. Consequently, the overall system is simplified compared with other heaters where feedback control should occur to prevent the temperature from being excessively increased.

With the vision assistance device according to the exemplary embodiment of the present invention, a transparent thin film containing carbon nanotubes is installed on the lens so that the fogging is prevented, and the facial area of the lens wearer is kept warm.

Furthermore, a portable power supply is installed at the frame together with a control switch so that the portability is improved and the operation is easily controlled.

The electric wire interconnecting the electrode and the portable power supply is connected to the electrode via a conductive adhesive so that the contact resistance is reduced. The electrode is connected to the conductive transparent thin film via a conductive adhesive layer so that the contact resistance is further reduced.

A transparent adhesive layer is formed between the lens and the conductive transparent thin film so that the conductive transparent thin film is stably fixed to the lens.

DESCRIPTION OF REFERENCE NUMERALS INDICATING PRIMARY ELEMENTS IN THE DRAWINGS

Figure 1:
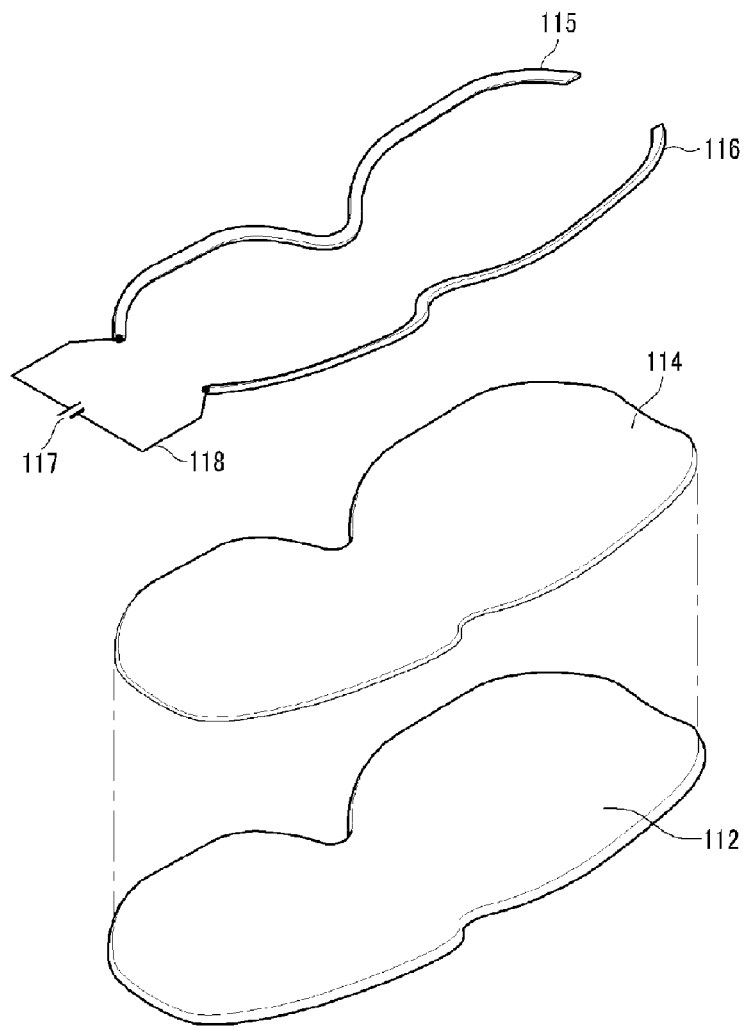
FIG. 1 is an exploded perspective view of a vision assistance device according to a first exemplary embodiment of the present invention.

112: lens
114: conductive transparent thin film
115, 116: electrode
117: portable power supply
118: electric wire
124: case
125: portable power supply
128: switch
162: conductive adhesive layer
163: conductive transparent thin film
164: transparent adhesive layer
167: transparent coating film

MODE FOR THE INVENTION

In this specification, the vision assistance device refers to a device that is placed in front of the eyes of a wearer for the wearer to see through built-in lens thereof, and includes goggles, vision assistance glasses, a lens-attached helmet, etc.

The present invention will be described more fully hereinafter with reference to the accompanying drawings, in which exemplary embodiments of the invention are shown. As those skilled in the art would realize, the described embodiments may be modified in various different ways, all without departing from the spirit or scope of the present invention. In the drawings, explanatorily irrelevant portions are omitted to clearly describe the present invention, and like reference numerals designate like elements throughout the specification.

Figure 2:
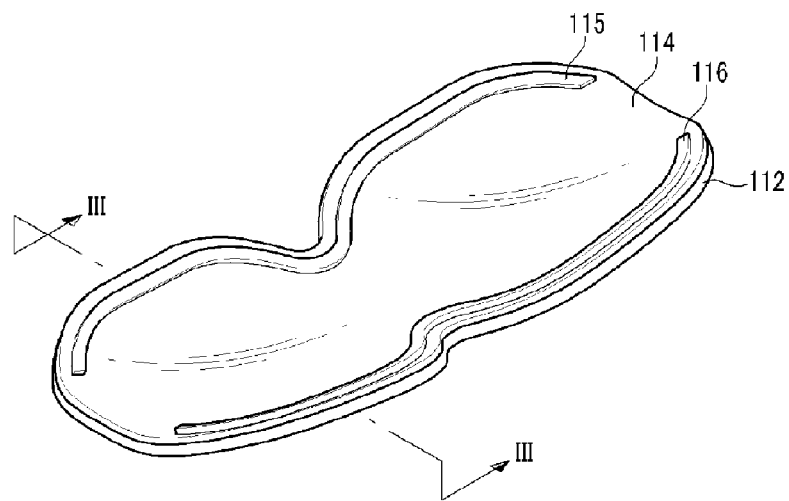
FIG. 2 is a perspective view of the vision assistance device shown in FIG. 1 where the members thereof are combined with each other.

FIG. 1 is an exploded perspective view of a vision assistance device according to a first exemplary embodiment of the present invention, and FIG. 2 is a perspective view of the vision assistance device shown in FIG. 1 where the members thereof are combined with each other.

Referring to FIG. 1 and FIG. 2, the vision assistance device according to the present exemplary embodiment includes a lens 112 based on a transparent material, a conductive transparent thin film 114 attached to the lens 112, electrodes 115 and 116 electrically connected to the conductive transparent thin film 114, and a portable power supply 117 electrically connected to the electrodes 115 and 116.

The lens 112 may be formed with a transparent material such as glass and a polymer. The lens 112 may be a magnifying lens, or goggles or helmet lens for protecting the eyes.

The conductive transparent thin film 114 has a structure where carbon nanotubes are interconnected. The carbon nanotubes are formed as pure carbon nanotubes, or as nanotubes doped or adsorbed with a metal oxide, a semiconductor, a metal, a polymer, or a semiconductor oxide. Such a material is combined with the carbon nanotubes so as to increase or decrease the conductivity thereof, thereby controlling the resistivity of the carbon nanotubes.

The conductive transparent thin film 114 has a transparency of 10% and electrical resistance of $1\Omega$ to $10^5\Omega$. The electrical resistance of the conductive transparent thin film 114 may be variously determined depending upon the thickness and usage of the lens.

The conductive transparent thin film 114 may be formed in various ways, for example, by way of vacuum filtration or spray coating. The carbon nanotubes are uniformly distributed on the surface of the lens while being connected to each other.

The conductive transparent thin film 114 is melted and pressed at a melting point or more so that it is stably fixed to the lens.

The electrodes 115 and 116 include a first electrode 115 disposed on a side of the lens 112, and a second electrode 116 spaced apart from the first electrode 115 on the lens 112 in the vertical direction, and are disposed such that they contact the edge of the conductive transparent thin film 114. The electrodes are located horizontally symmetrical to each other with respect to a vertical center line of the lens. This is to uniformly heat the lens that is structured to be horizontally symmetrical.

The electrodes 115 and 116 may be formed with a material such as platinum, copper, and silver.

Accordingly, when connected with a power supply, current flow occurs from the first electrode 115 to the second electrode 116 through the conductive transparent thin film 114, and in this process, heat is generated due to the resistance of the conductive transparent thin film 114. Particularly, the conductive transparent thin film 114 containing carbon nanotubes is quickly heated to a predetermined temperature so as to maintain the temperature of the lens 112 at a predetermined degree without any other controllers.

Accordingly, it becomes possible to easily prevent fogging from occurring on the lens due to the difference in temperature between the lens and the interior of the lens under the low-temperature atmosphere.

The portable power supply 117 is connected to the electrodes 115 and 116. The portable power supply 117 may be formed with a small mercury battery, a rechargeable battery, or a solar battery. The portable power supply 117 is connected to the electrodes 115 and 116 via electric wires 118. The portable power supply 117 may be fixed to a frame (not shown) for fixing the lens 112. Particularly when the portable power supply 117 is formed with a solar battery, a current collecting plate may be installed on the outer surface of the frame.

Figure 3:
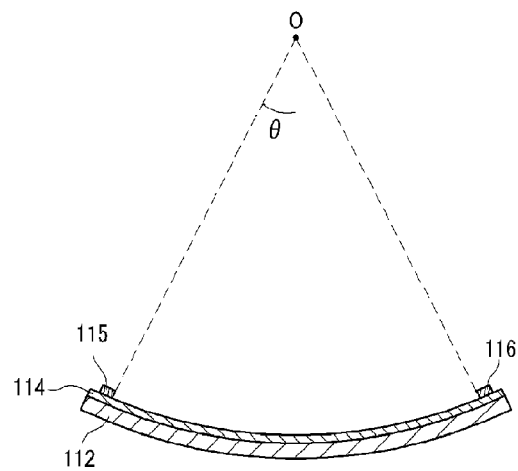
FIG. 3 is a cross-sectional view of the vision assistance device shown in FIG. 2 taken along the III-III line thereof.

FIG. 3 is a cross-sectional view of the vision assistance device shown in FIG. 2 taken along the III-III line thereof. Referring to FIG. 3, when the center of the eye is indicated by O, the angle θ of the line proceeding from O to the vertical center of the lens 112 to the line proceeding from O to the electrodes 115 and 116 is established to be 10° or more.

When θ is established to be less than 10°, the electrodes 115 and 116 obstruct the lens wearer's field of vision so as to cause inconvenience.

Figure 4:
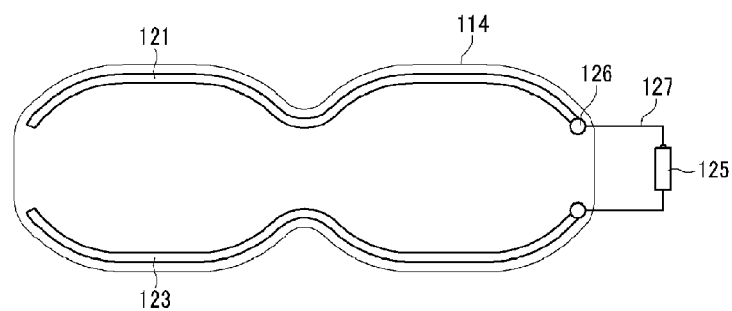
FIG. 4 is a top plan view of a vision assistance device according to a second exemplary embodiment of the present invention.

FIG. 4 is a top plan view of a vision assistance device according to a second exemplary embodiment of the present invention. Referring to FIG. 4, the vision assistance device according to the present exemplary embodiment includes a lens, a conductive transparent thin film 114, a first electrode 121, a second electrode 123 spaced apart from the first electrode 121 by a distance, and a portable power supply 125 connected to the first and second electrodes 121 and 123 via electric wires 127. The electric wires 127 are connected to the first and second electrodes 121 and 123 via a conductive adhesive 126. The conductive adhesives 126 may be formed with silver (Ag) paste, lead, etc. As with the present exemplary embodiment, when the electrodes 121 and 123 and the electric wires 127 are connected to each other via the conductive adhesive 126, the contact resistance therebetween is reduced.

Figure 5:
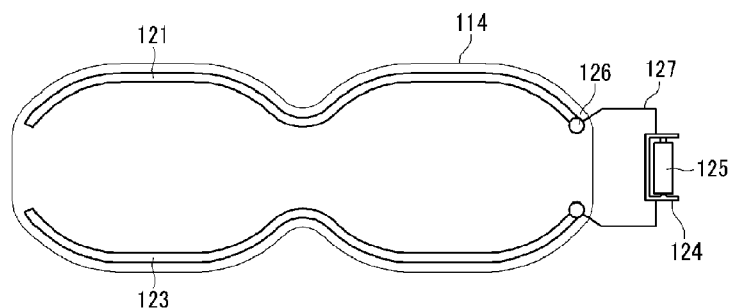
FIG. 5 is a top plan view of a vision assistance device according to a third embodiment of the present invention.

FIG. 5 is a top plan view of a vision assistance device according to a third exemplary embodiment of the present invention. Referring to FIG. 5, the vision assistance device according to the present exemplary embodiment includes a case 124 to which a portable power supply 125 is fitted. The portable power supply 125 is connected to electric wires 127 via the case 124. The electric wires 127 are insulated.

The case 124 may be a part of a frame for supporting the lens, or the case 124 may be fixed to the frame.

Figure 6:
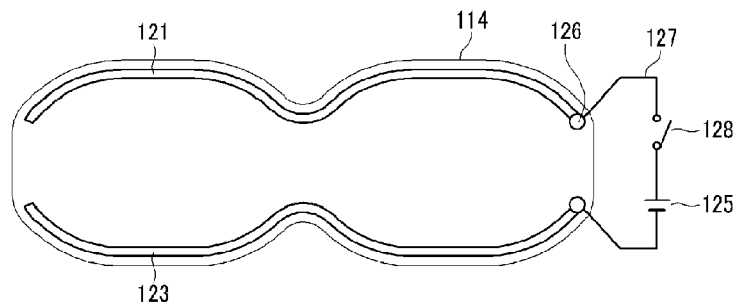
FIG. 6 is a top plan view of a vision assistance device according to a fourth exemplary embodiment of the present invention.

FIG. 6 is a top plan view of a vision assistance device according to a fourth exemplary embodiment of the present invention. As shown in FIG. 6, a switch 128 is installed between a portable power supply 125 and electrodes 121 and 123 to control the flow of electrical current. The switch 128 controls the connection between the electrodes 121 and 123 and the portable power supply 125 such that the power is supplied to the electrodes 121 and 123 according to the desire of the wearer.

Figure 7:
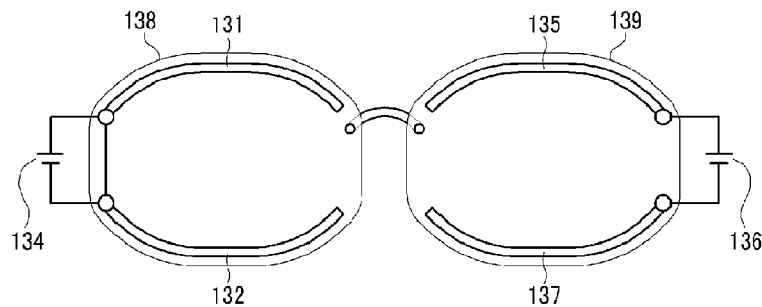
FIG. 7 is a top plan view of a vision assistance device according to a fifth exemplary embodiment of the present invention.

FIG. 7 is a top plan view of a vision assistance device according to a fifth exemplary embodiment of the present invention.

As shown in FIG. 7, the vision assistance device according to the present exemplary embodiment includes first and second electrodes 131 and 132 spaced apart from each other in the vertical direction, and third and fourth electrodes 135 and 137 spaced apart from the electrodes 131 and 132 in the horizontal direction. With the present exemplary embodiment, two lenses 138 and 139 are provided like usual vision assistance glasses, and accordingly, the electrodes corresponding thereto are arranged side by side while being spaced apart from each other by a distance. A first portable power supply 134 is connected to the first and second electrodes 131 and 132, and a second portable power supply 136 is connected to the third and fourth electrodes 135 and 137. The portable power supplies 134 and 136 supply power to respective electrodes 131, 132, 135, and 137 connected thereto.

Figure 8:
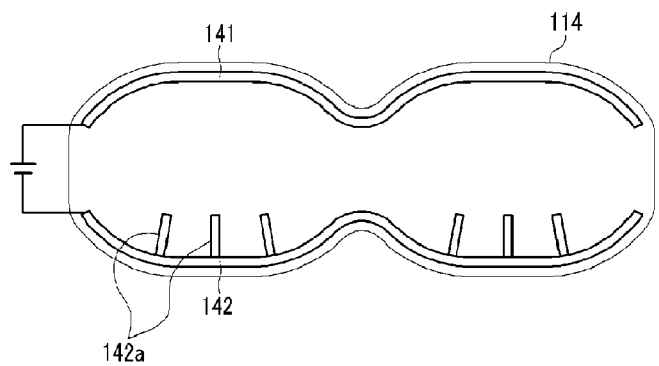
FIG. 8 is a top plan view of a vision assistance device according to a sixth exemplary embodiment of the present invention.

FIG. 8 is a top plan view of a vision assistance device according to a sixth exemplary embodiment of the present invention. As shown in FIG. 8, the vision assistance device according to the present exemplary embodiment includes a first electrode 141, and a second electrode 142 spaced apart from the first electrode 141 by a distance. The electrodes 141 and 142 are electrically connected to a power supply. A plurality of electrode protrusions 142a are formed at the second electrode 142 such that they are protruded to the inner side of the lens. As the electric current is inclined to flow the shortest distance, it collectively flows along the narrow region between the electrodes 141 and 142, and accordingly, much heat is generated at that region. In order to solve such a problem, with the present exemplary embodiment, a plurality of electrode protrusions 142a are formed at the second electrode 142 such that the electric current flows from the ends of the electrode protrusions 142a to the first electrode 141. With this structure, the current flow is diversified so that the lens can be heated uniformly. It is exemplified with the present exemplary embodiment that the electrode protrusions 142a are formed at the second electrode 142, but such electrode protrusions may be formed at the first electrode 141.

Figure 9:
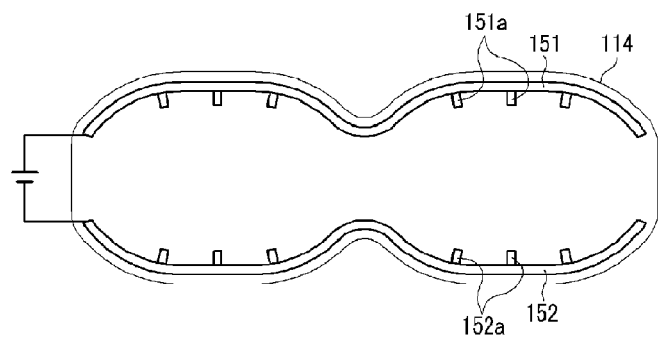
FIG. 9 is a top plan view of a vision assistance device according to a seventh exemplary embodiment of the present invention.

FIG. 9 is a top plan view of a vision assistance device according to a seventh exemplary embodiment of the present invention. Referring to FIG. 9, the vision assistance device according to the present exemplary embodiment includes a first electrode 151, and a second electrode 152 spaced apart from the first electrode 151 by a distance. The electrodes 151 and 152 are electrically connected to a power supply. A plurality of electrode protrusions 151a and 152a are formed at the first and second electrodes 151 and 152 such that they are protruded to the inner side of the lens. With the present exemplary embodiment, the plurality of electrode protrusions 151a and 152a are formed at the first and second electrodes 151 and 152, respectively. Accordingly, the electrode protrusions 151a and 152a are prevented from being overly protruded to the inner side of the lens 141, and do not obstruct the wearer's field of vision.

Figure 10:
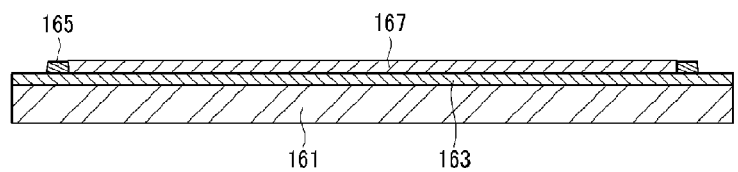
FIG. 10 is a top plan view of a vision assistance device according to an eighth exemplary embodiment of the present invention.

FIG. 10 is a cross-sectional view of a vision assistance device according to an eighth exemplary embodiment of the present invention. As shown in FIG. 10, the vision assistance device according to the present exemplary embodiment includes a lens 161, a conductive transparent thin film 163 formed on a surface of the lens 161, electrodes 165 formed on the conductive transparent thin film 163, and a transparent coating film 167 formed on the conductive transparent thin film 163. The transparent coating film 167 may be formed between the electrodes 165, or may cover the entire surface of the conductive transparent thin film 163. If the transparent coating film 167 covers the entire surface of the conductive transparent thin film 163, electric wires are first connected to the electrodes 165, and the transparent coating film 167 is then formed.

The transparent coating film is formed with an insulating transparent material so as to insulate the conductive transparent thin film from the outside.

Figure 11:
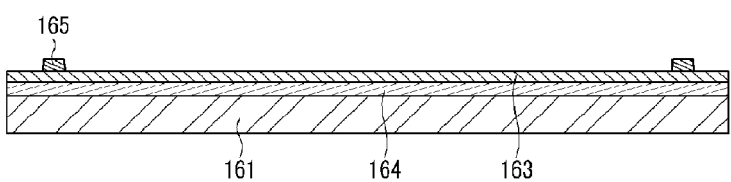
FIG. 11 is a top plan view of a vision assistance device according to a ninth exemplary embodiment of the present invention.

FIG. 11 is a cross-sectional view of a vision assistance device according to a ninth exemplary embodiment of the present invention. As shown in FIG. 11, the vision assistance device according to the present exemplary embodiment includes a transparent adhesive layer 164 interposed between a lens 161 and a conductive transparent thin film 163. The transparent adhesive layer 164 is formed with a commercially available transparent adhesive, and has a role of stably fixing the conductive transparent thin film 163 to the lens 161.

Figure 12:
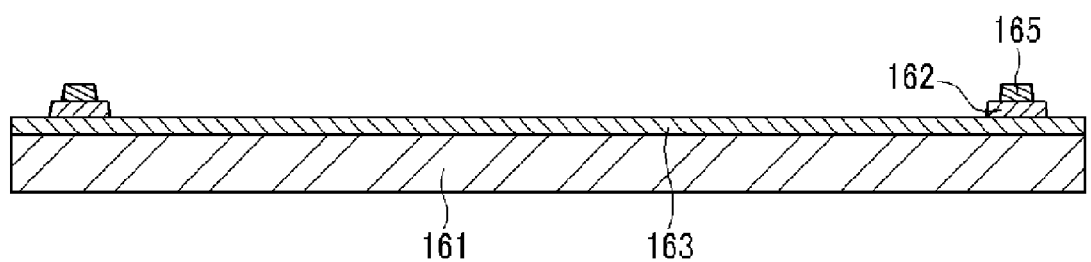
FIG. 12 is a top plan view of a vision assistance device according to a tenth exemplary embodiment of the present invention.

FIG. 12 is a cross-sectional view of a vision assistance device according to a tenth exemplary embodiment of the present invention. As shown in FIG. 12, a conductive adhesive layer 162 is formed between the conductive transparent thin film 163 and each of the electrodes 165. The conductive adhesive layer 162 reduces the contact resistance between the conductive transparent thin film 163 and the electrode 165.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

The invention claimed is:

1. A vision assistance device with a transparent heater comprising:
    a lens based on a transparent material;
    a conductive transparent thin film surface-contacting the lens and containing carbon nanotubes;
    electrodes electrically connected to the conductive transparent thin film; and
    a portable power supply electrically connected to the electrodes,
    wherein the electrode has electrode protrusions protruded to the inner side of the lens.

2. The vision assistance device of claim 1, wherein the conductive transparent thin film has transparency of 10% or more.

3. The vision assistance device of claim 1, wherein the conductive transparent thin film has electrical resistance of $1\Omega$ to $10^5\Omega$.

4. The vision assistance device of claim 1, wherein the carbon nanotubes are adsorbed with a material selected from the group consisting of a metal oxide, a semiconductor, a metal, a polymer, and a semiconductor oxide, or a combination thereof.

5. The vision assistance device of claim 1, wherein the lens is formed with glass or a polymer.

6. The vision assistance device of claim 1, wherein the electrode is installed at a location where the angle of a line proceeding from the eye center of the lens wearer to the vertical center of the lens to the line proceeding from the eye center of the lens wearer to the electrode reaches 10° or more.

7. The vision assistance device of claim 1, wherein the portable power supply is electrically connected to the electrode via an electric wire.

8. The vision assistance device of claim 7, wherein the portable power supply is fitted to a case and electrically connected to the electric wire via the case.

9. The vision assistance device of claim 7, wherein the electric wire is connected to the electrode via a conductive adhesive.

10. The vision assistance device of claim 1, wherein the portable power supply is a portable solar battery.

11. The vision assistance device of claim 1, wherein the electrodes are spaced apart from each other by a distance in the vertical direction of the lens.

12. The vision assistance device of claim 1, wherein the electrodes are horizontally symmetrical to each other with respect to a vertical center line of the lens.

13. The vision assistance device of claim 1, wherein the conductive transparent thin film is attached to the lens via a transparent adhesive layer.

14. The vision assistance device of claim 1, wherein a switch is installed between the electrode and the portable power supply.

15. The vision assistance device of claim 1, wherein an insulating transparent coating film is formed on the conductive transparent thin film.

16. The vision assistance device of claim 1, wherein a conductive adhesive layer is formed between the conductive transparent thin film and the electrode.

* * * * *